(12) United States Patent
Braun

(10) Patent No.: US 9,825,331 B2
(45) Date of Patent: Nov. 21, 2017

(54) FLUORINATED DERIVATIVES OF MELDRUM'S ACID, A METHOD FOR THE PREPARATION OF THE SAME, AND THEIR USE AS A SOLVENT ADDITIVE

(71) Applicant: SOLVAY SA, Brussels (BE)

(72) Inventor: Max Josef Braun, Wedemark (DE)

(73) Assignee: SOLVAY SA, Brussels (BE)

( * ) Notice: Subject to any disclaimer, the term of this patent is extended or adjusted under 35 U.S.C. 154(b) by 165 days.

(21) Appl. No.: 14/360,682

(22) PCT Filed: Nov. 23, 2012

(86) PCT No.: PCT/EP2012/073424
§ 371 (c)(1),
(2) Date: May 27, 2014

(87) PCT Pub. No.: WO2013/079397
PCT Pub. Date: Jun. 6, 2013

(65) Prior Publication Data
US 2014/0322618 A1   Oct. 30, 2014

(30) Foreign Application Priority Data
Nov. 30, 2011  (EP) .................................... 11191337

(51) Int. Cl.
| | | |
|---|---|---|
| H01M 10/0567 | (2010.01) | |
| H01M 10/052 | (2010.01) | |
| H01M 12/02 | (2006.01) | |
| H01M 12/06 | (2006.01) | |
| H01M 12/08 | (2006.01) | |
| H01M 10/0569 | (2010.01) | |
| C07D 319/06 | (2006.01) | |

(52) U.S. Cl.
CPC ...... *H01M 10/0567* (2013.01); *C07D 319/06* (2013.01); *H01M 10/052* (2013.01); *H01M 10/0569* (2013.01); *H01M 12/02* (2013.01); *H01M 12/06* (2013.01); *H01M 12/08* (2013.01); *Y02E 60/128* (2013.01)

(58) Field of Classification Search
CPC ................................................ H01M 10/0567
See application file for complete search history.

(56) References Cited

U.S. PATENT DOCUMENTS

| | | | |
|---|---|---|---|
| 2,859,245 A | 11/1958 | Smith | |
| 4,003,807 A | 1/1977 | Childs et al. | |
| 5,481,029 A | 1/1996 | Braun et al. | |
| 5,916,708 A | 6/1999 | Besenhard et al. | |
| 6,159,640 A | 12/2000 | Appel et al. | |
| 6,365,068 B1 * | 4/2002 | Michot | B01J 31/0215 252/500 |
| 6,489,064 B2 | 12/2002 | Appel et al. | |
| 6,677,085 B2 | 1/2004 | Appel et al. | |
| 7,145,046 B2 | 12/2006 | Braun et al. | |
| 7,906,235 B2 | 3/2011 | Michot et al. | |
| 2005/0214184 A1 | 9/2005 | Chambers et al. | |
| 2011/0021522 A1 * | 1/2011 | Wells | C07D 311/12 514/233.5 |

FOREIGN PATENT DOCUMENTS

| | | | |
|---|---|---|---|
| CN | 1775773 A | 5/2006 | |
| DE | 4120704 A1 | 12/1992 | |
| DE | 19945890 A1 | 4/2000 | |
| EP | 0850932 A1 | 7/1998 | |
| JP | 09301928 A | * 11/1997 | |
| JP | H9-301928 A | 11/1997 | |
| JP | 11260402 A | 9/1999 | |
| JP | 2003330195 A | 11/2003 | |
| JP | 2005-525229 A | 8/2005 | |
| JP | 2005317403 A | * 11/2005 | |
| WO | 2007042471 A1 | 4/2007 | |

OTHER PUBLICATIONS

JP09301928A Translation from Espacenet.*
David Davidson & AI J. Am. Chem. Soc. vol. 70, 1948, pp. 3426-3428.

* cited by examiner

*Primary Examiner* — Barbara Gilliam
*Assistant Examiner* — Nathanael Zemui

(57) ABSTRACT

Disclosed are certain fluorinated derivatives of Meldrum's acid as novel compounds, preparation methods for the same, their use in Li ion batteries, Li air batteries and Li sulphur batteries as well as solvent compositions, electrolyte compositions and respective batteries containing them.

12 Claims, No Drawings

FLUORINATED DERIVATIVES OF MELDRUM'S ACID, A METHOD FOR THE PREPARATION OF THE SAME, AND THEIR USE AS A SOLVENT ADDITIVE

This application is a U.S. national stage entry under 35 U.S.C. §371 of International Application No. PCT/EP2012/073424 filed Nov. 23, 2012, which claims priority to European patent application No. 11191337.2 filed on Nov. 30, 2011. The entire contents of these applications are explicitly incorporated herein by this reference.

The invention concerns certain fluorinated derivatives of Meldrum's acid, methods for their preparation and their use as an additive for Li ion batteries.

Li ion batteries, Li air batteries and Li sulfur batteries are well-known rechargeable means for storing electric energy. The advantage of this type of batteries is, for example, a high energy density, and they have no memory effect.

Li ion batteries comprise an anode, a cathode and an electrolyte composition containing a solvent, an conductive salt and often additives. The solvent is an aprotic organic solvent which serves to dissolve the conductive salt. See, for example, WO 2007/042471 which provides information concerning suitable solvents. Suitable conducting salts are known in the art. $LiPF_6$ is the preferred conducting salt. Other conducting salts are also suitable as constituent of the electrolyte solutions of the present invention, for example, e.g. lithium bisoxalatoborate (LiBOB), lithium bis(fluorosulfonyl)imide (LiFSI), lithium bis(trifluorsulfonyl)imide (LiTFSI) or $LiBF_4$.

Additives improve the properties of the Li ion batteries, e.g. the life of the battery or to reduce the flammability. For example, $LiPO_2F_2$ is applicable as additive. Fluorinated organic compounds, for example, fluorinated cyclic carbonates, improve the life of the battery and reduce the flammability of the solvent.

Object of the present invention is to provide further additives for Li ion batteries. This object, and other objects, are achieved by the invention as outlined in the description and the claims.

One aspect of the present invention concerns compounds which are derivatives of Meldrum's acid and are represented by formula (I):

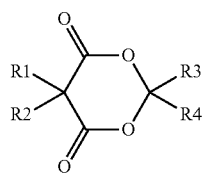

Formula (I)

wherein R1 and R2 independently denote hydrogen, halogen, or linear or branched alkyl group optionally substituted by one or more halogen atoms; and
wherein R3 and R4 independently denote hydrogen, halogen, or linear or branched alkyl group optionally substituted by one or more halogen atom;
provided that at least one of the R1 to R4 is fluorine or fluorinated substituent.

In the context of the present invention, the term "comprising" is intended to mean also "consisting of". The plural is intended to include the singular, and vice versa.

Compounds of formula (I) are preferred wherein the halogen is fluorine.

Preferably, R1 is fluorine.
Preferably, R2 is hydrogen or fluorine.
More preferably, R1 is fluorine and R2 is hydrogen.
Preferably, R3 and R4 are the same or different and are independently selected from the group consisting of fluorine, methyl, ethyl, and methyl and ethyl substituted by at least one fluorine atom. More preferably, R3 and R4 are independently selected from the group consisting of fluorine, methyl, mono fluoromethyl, difluoromethyl and trifluoromethyl.

Especially preferred compounds are those of formula (I-1), (I-2), (I-3) or (I-4).

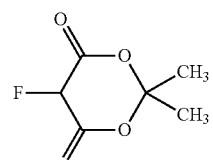

Formula (I-1)

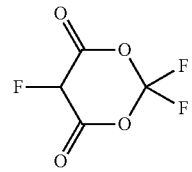

Formula (I-2)

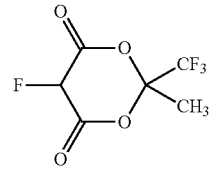

Formula (I-3)

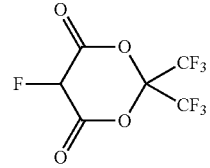

Formula (I-4)

Another aspect of the present invention is to provide a method for the manufacture of the compounds of formula (I).

The manufacture can be performed according to several embodiments. Generally, the compounds may be prepared analogously to the manufacture of Meldrum's acid from a compound with a keto group and malonic acid. Suitable starting compounds having a keto group are especially acetone, methyl ethyl ketone and diethyl ketone; and malonic acid or their halogenated or fluorinated derivatives.

According to a first preferred embodiment, at least one starting compound contains at least one fluorine atom as a substituent; optionally, but this is not preferred, at least one of the starting compounds may be substituted by a halogen atom.

According to a second embodiment, at least one starting compound is substituted by at least one halogen atom which is not fluorine; after the condensation reaction of the starting compounds, the halogen atom, especially chlorine, is substituted by fluorine, e.g. in well-known chlorine-fluorine exchange reactions with fluorinating agents like metal fluorides, e.g. CsF or KF, or HF adducts of amines, e.g. HF adducts of trialkylamines or HF adducts of aromatic amines like pyridine.

According to a third embodiment, non-fluorinated starting compounds are applied, and the resulting Meldrum acid or Meldrum acid derivative are post fluorinated e.g. with electrophilic fluorinating agents, e.g. N-fluorosulfonamides to substitute F for H at the C(O)—CH$_2$—C(O) group. H atoms at the alkyl group or alkyl groups of the O—C (R1R2)-O function can be substituted by F using via electrochemical fluorination or by a reaction with elemental F$_2$, preferably at low temperatures in an inert solvent, e.g. perfluorinated carbon compounds, and using F$_2$ diluted with inert gas such as N$_2$. This embodiment is especially suitable for compounds of formula (I) in which R1 is F and R2 is H or F and R3 and R4 are H or F.

The first embodiment is preferred and will now be explained in detail.

To manufacture compounds of formula (I) in which R3 and R4 are methyl, ethyl, or methyl or ethyl substituted by at least one F atom, compounds of formula (II), R3-C(O)—R4, are applied as starting material. R3 and R4 are methyl or ethyl groups at least one of which is substituted by at least one F atom. These compounds can be manufactured from acetone, butanone or pentanone, optionally substituted by one or more fluorine atoms by electrochemical fluorination as is described in U.S. Pat. No. 4,003,807. The process described is that US patent is mainly designed to produce perfluorinated ketones but respective monofluorinated and polyfluorinated ketones are produced, too, and by applying respective shorter reaction times, the yield of monofluorinated or polyfluorinated ketones can be optimized.

Partially and polyfluorinated ketones can also be manufactured from β-ketoester compounds by decarboxylation initiated by acids, for example, by sulfonic acids, mineral acids or trifluoroacetic acid, as described in U.S. Pat. No. 5,481,029.

Compounds which have a C—(O)—CFH—C(O) group or a C—(O)—CF$_2$—C(O) group in the ring can be prepared by applying monofluorinated or difluorinated malonic acid as a starting material. Monofluoromalonic acid and difluoromalonic acid can be prepared from the respective chloro-substituted malonic acid ester and fluorinating agents, e.g. using the HF adducts of pyridine, diazabicyclononene ("DBN") or diazabicycloundecene ("DBU") with subsequent saponification of the ester groups. The manufacture of mono fluorinated and difluorinated malonic acid esters from respective chlorinated esters by chlorine-fluorine exchange reactions using the adducts of HF and amines as fluorinating agent is described in U.S. Pat. No. 7,145,046 the whole content of which is incorporated herein for all purposes.

Another aspect of the present invention concerns the manufacture of the compounds of formula (I).
According to this aspect, a process, a method for the preparation of compounds which are a fluorinated derivative of the Meldrum's acid having formula (I)

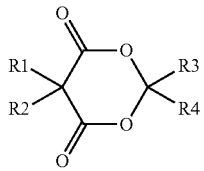

Formula (I)

Is provided, comprising the reaction of malonic acid or fluoromalonic acid having the formula HO(O)C—CR1R2-C(O)OH wherein R1 and R2 independently denote hydrogen, halogen, or linear or branched alkyl group optionally substituted by one or more halogen atoms, with a ketone having the formula R3-C(O)—R4 wherein R3 and R4 independently denote a linear or branched alkyl group optionally substituted by one or more halogen atoms, or to produce compounds of formula (I) wherein R3 and R4 are F, by reacting malonic acid or fluoromalonic acid having the formula HO(O)C—CR1R2-C(O)OH wherein R1 and R2 independently denote hydrogen, halogen, or linear or branched alkyl group optionally substituted by one or more halogen atoms, with C(O)Cl$_2$ or C(O)F$_2$, and reacting the intermediate 2,4,6-trione compound with SF$_4$, or to produce compounds of formula (I) wherein R3 is F and R4 is H, by reacting malonic acid or fluoromalonic acid having the formula HO(O)C—CR1R2-C(O)OH wherein R1 and R2 independently denote hydrogen, halogen, or linear or branched alkyl group optionally substituted by one or more halogen atoms, with C(O)Cl$_2$ or C(O)F$_2$, reacting the intermediate 2,4,6-trione compound with a reducing agent, especially hydrogen, to produce the respective C4-hydroxy compound, and reacting said C4-hydroxy compound with SF$_4$ to obtain compounds of formula (I) wherein R3 is F and R4 is H.

In the following, the manufacture of preferred fluorosubstituted derivatives of Meldrum's acid is described. The starting compounds are esters. They can be hydrolyzed to form the respective acid by basic or acidic hydrolysis. The hydrolysis can be performed as described in DE Offenlegungsschrift 4120704, e.g. from the dimethylester and NaOH in water and subsequent contact with an ion exchange resin, e.g. Lewatit S 100. This step is followed by a condensation reaction which may be catalyzed by sulfuric acid. The condensation reaction can be performed in analogy of the preparation of Meldrum's acid by David Davidson and Sidney A. Bernhard in J. Am. Chem. Soc. 70 (1948), pages 3426 to 3428, and especially on page 3428, left column. If desired, dehydrating agents, for example, acetic acid anhydride can be applied to shift the equilibrium of the condensation reaction.

Manufacture of 5-fluoro-2-methyl-2-trifluormethyl-1,3-dioxane-4,6-dione

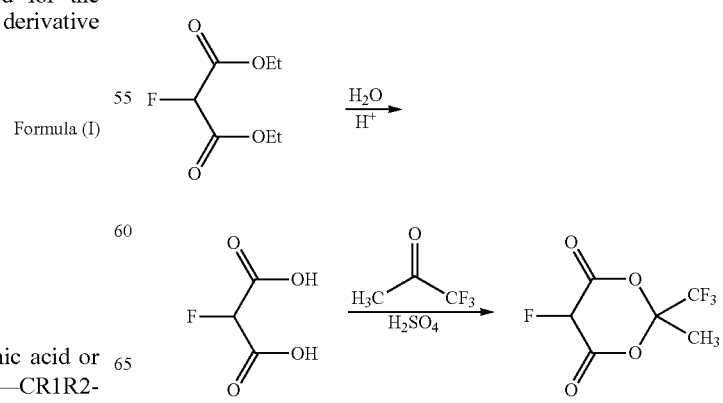

Manufacture of 5-fluoro-2,2-bistrifluormethyl-1,3-dioxane-4,6-dione

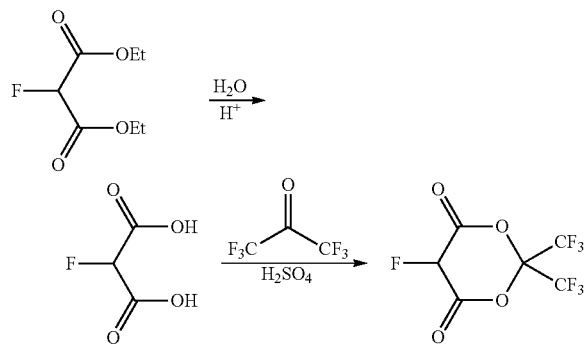

Manufacture of 2-methyl-2-trifluormethyl-1,3-dioxane-4,6-dione

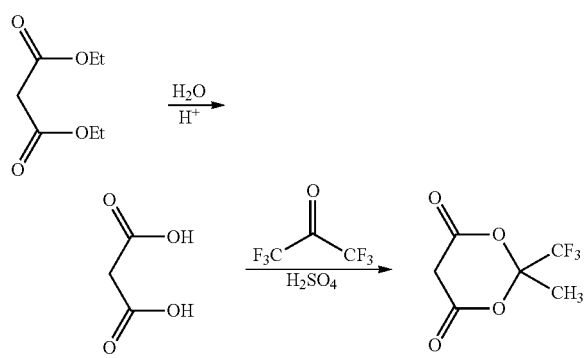

Manufacture of 2,2-bistrifluormethyl-1,3-dioxane-4,6-dione

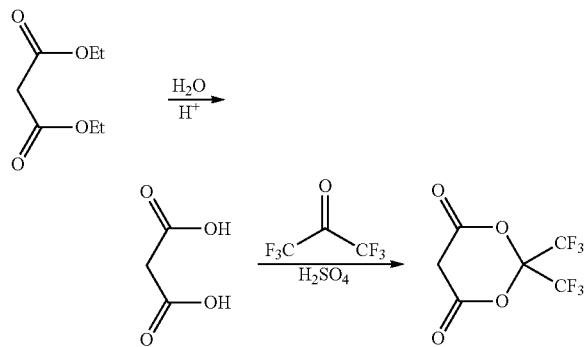

The following reaction equation indicates a way how to prepare 2,2,5-trifluoro-1,3-dioxane-4,6-dione. The first step provides fluoromalonic acid from the respective diester by hydrolysis. In the second step, 5-fluoro-1,3-dioxane-2,4,6-trione is produced as intermediate compound by reaction of fluoromalonic acid and $C(O)Cl_2$. The last step provides for the desired compound 2,2,5-trifluoro-1,3-dioxane-4,6-dione by transforming the keto group into a $CF_2$ group by reacting the intermediate compound with $SF_4$. This can be performed as described in U.S. Pat. No. 2,859,245. Additionally or instead of $SF_4$ (which is a gas), a derivative of SF4 can be applied, especially $R_2NSF_3$ wherein R is an alkyl group, especially with 1 to 3 C atoms. A representative compounds is diethylamino-$SF_3$ ("DAST"). Another fluorinating agent of this type is Deoxo-Fluor® which has the formula $(CH_3OCH_2CH_2)_2NSF_3$ and is available from Aldrich.

A suitable way to manufacture 2,5-difluoro-1,3-dioxane-2,4,6-trione:

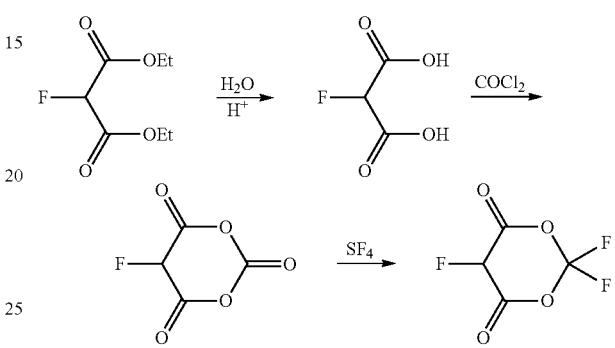

To obtain 2,5-difluoro-1,3-dioxane-2,4,6-trione, the intermediate 5-fluoro-1,3-dioxane-2,4,6-trione can be reacted with hydrogen to reduce the 5-keto group into a 5-hydroxy group which then can be reacted with $SF_4$ to form the respective C5-mono fluorinated bridging group.

The compounds can be isolated by methods known in the art, for example, by distillation, chromatography, extraction and the like.

Another aspect of the present invention concerns the use of the compounds of formula (I)

Formula (I)

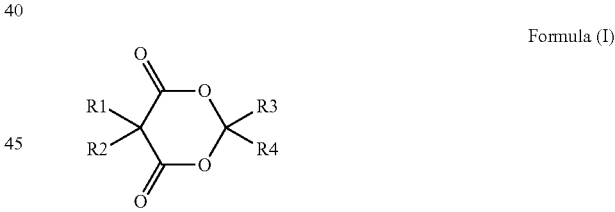

wherein R1 to R4 independently denote hydrogen, halogen, or linear or branched alkyl group optionally substituted by one or more halogen atoms; provided that at least one of the R1 to R4 is fluorine or fluorinated substituent, as a solvent or, preferably, as an additive solvents or electrolyte compositions useful for rechargeable batteries, especially those rechargeable batteries containing the $Li^+$ ion as conductive salt, especially Li ion batteries, Li air batteries and Li sulfur batteries.

For this use, compounds of formula (I) are preferred wherein the halogen is fluorine.

Preferably, R1 is fluorine.

Preferably, R2 is hydrogen or fluorine.

More preferably, R1 is fluorine and R2 is hydrogen.

Preferably, R3 and R4 are the same or different and are independently selected from the group consisting of fluorine, methyl, ethyl, and methyl and ethyl substituted by at least one fluorine atom. More preferably, R3 and R4 are independently selected from the group consisting of fluorine, methyl, monofluoromethyl, difluoromethyl and trifluoromethyl.

Especially preferably, compounds of formula (I-1), (I-2), (I-3) or (I-4) are used:

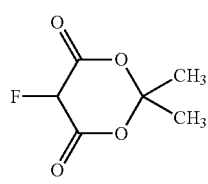

Formula (I-1)

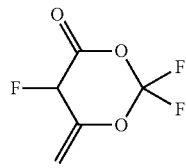

Formula (I-2)

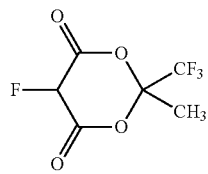

Formula (I-3)

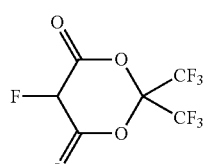

Formula (I-4)

Likewise, compounds which are analogous to the compounds of formulae (I-2) to (I-4) are applied which are not substituted by fluorine on the C-2 carbon atom.

Often, they will be applied as an additive in an amount which is greater than 0 and preferably equal to or lower than 15% by weight relative to the total electrolyte composition including other solvents, the electrolyte salt and other additives if other additives are present. Preferably, they are present in an amount equal to or greater than 2% by weight relative to the total electrolyte composition. Preferably, they are present in the electrolyte composition in an amount of equal to or lower than 10% by weight relative to the total weight of the electrolyte composition. The term "total electrolyte composition" denotes compositions containing at least one Meldrum acid derivative compound of formula (I) of the invention, an electrolyte salt and preferably at least one further solvent and optionally further additives.

Compounds of formula (I) are often applied together with at least one solvent. Aprotic solvents suitable for use in Li ion batteries, Li air batteries and Li sulfur batteries are known.

Suitable solvents (which generally are aprotic organic solvents) are known to the expert in the field of Li ion batteries. For example, organic carbonates, but also lactones, formamides, pyrrolidinones, oxazolidinones, nitroalkanes, N,N-substituted urethanes, sulfo lane, dialkyl sulfoxides, dialkyl sulfites, acetates, nitriles, acetamides, glycol ethers, dioxolanes, dialkyloxyethanes, trifluoroacetamides, are very suitable as solvents.

Preferably, the aprotic organic solvent is selected from the group of dialkyl carbonates (which are linear) and alkylene carbonates (which are cyclic), and wherein the term "alkyl" denotes preferably C1 to C4 alkyl, the term "alkylene" denotes preferably C2 to C7 alkylene groups, including a vinylidene group, wherein the alkylene group preferably comprises a bridge of 2 carbon atoms between the oxygen atoms of the —O—C(O)—O— group; ketones, nitriles and formamides. Dimethyl formamide, carboxylic acid amides, for example, N,N-dimethyl acetamide and N,N-diethyl acetamide, acetone, acetonitrile, linear dialkyl carbonates, e.g. dimethyl carbonate, diethyl carbonate, methyl ethyl carbonate, cyclic alkylene carbonates, e.g. ethylene carbonate, propylene carbonate, and vinylidene carbonate, are suitable solvents.

Fluorosubstituted compounds different from the compounds of formula (I) mentioned above, for example, fluorinated carbonic esters which are selected from the group of fluorosubstituted ethylene carbonates, polyfluorosubstituted dimethyl carbonates, fluorosubstituted ethyl methyl carbonates, and fluorosubstituted diethyl carbonates are other solvents or, preferably, suitable additives or in the electrolytic compositions. Preferred fluorosubstituted carbonates are monofluoroethylene carbonate, 4,4-difluoro ethylene carbonate, 4,5-difluoro ethylene carbonate, 4-fluoro-4-methyl ethylene carbonate, 4,5-difluoro-4-methyl ethylene carbonate, 4-fluoro-5-methyl ethylene carbonate, 4,4-difluoro-5-methyl ethylene carbonate, 4-(fluoromethyl)-ethylene carbonate, 4-(difluoromethyl)-ethylene carbonate, 4-(trifluoromethyl)-ethylene carbonate, 4-(fluoromethyl)-4-fluoro ethylene carbonate, 4-(fluoromethyl)-5-fluoro ethylene carbonate, 4-fluoro-4,5-dimethyl ethylene carbonate, 4,5-difluoro-4,5-dimethyl ethylene carbonate, and 4,4-difluoro-5,5-dimethyl ethylene carbonate; dimethyl carbonate derivatives including fluoromethyl methyl carbonate, difluoromethyl methyl carbonate, trifluoromethyl methyl carbonate, bis(difluoro)methyl carbonate, and bis(trifluoro)methyl carbonate; ethyl methyl carbonate derivatives including 2-fluoroethyl methyl carbonate, ethyl fluoromethyl carbonate, 2,2-difluoroethyl methyl carbonate, 2-fluoroethyl fluoromethyl carbonate, ethyl difluoromethyl carbonate, 2,2,2-trifluoroethyl methyl carbonate, 2,2-difluoroethyl fluoromethyl carbonate, 2-fluoroethyl difluoromethyl carbonate, and ethyl trifluoromethyl carbonate; and diethyl carbonate derivatives including ethyl (2-fluoroethyl)carbonate, ethyl (2,2-difluoroethyl)carbonate, bis(2-fluoroethyl) carbonate, ethyl (2,2,2-trifluoroethyl)carbonate, 2,2-difluoroethyl 2'-fluoroethyl carbonate, bis(2,2-difluoroethyl) carbonate, 2,2,2-trifluoroethyl 2'-fluoroethyl carbonate, 2,2,2-trifluoroethyl 2',2'-difluoroethyl carbonate, and bis(2,2,2-trifluoroethyl)carbonate, 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-fluoro-4,5-divinylethylene carbonate, 4,5-difluoro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate and 4,5-difluoro-4,5-diphenylethylene carbonate, fluoromethyl phenyl carbonate, 2-fluoroethyl phenyl carbonate, 2,2-difluoroethyl phenyl carbonate and 2,2,2-trifluoroethyl phenyl carbonate, fluoromethyl vinyl carbonate, 2-fluoroethyl vinyl carbonate, 2,2-difluoroethyl vinyl carbonate and 2,2,2-trifluoroethyl vinyl carbonate, fluoromethyl allyl carbonate, 2-fluoroethyl allyl carbonate, 2,2-difluoroethyl allyl carbonate and 2,2,2-trifluoroethyl allyl carbonate are mentioned as suitable components of electrolyte solutions of the invention.

Other suitable additives useful in the electrolyte compositions according to the present invention are those described in WO2007/042471 selected from the group of aromatic compounds consisting of 1-acetoxy-2-fluorobenzene, 1-acetoxy-3-fluorobenzene, 1-acetoxy-4-fluorobenzene, 2-acetoxy-5-fluorobenzyl acetate, 4-acetyl-2,2-difluoro-1,3-benzodioxole, 6-acetyl-2,2,3,3-tetrafluorobenzo-1,4-dioxin, 1-acetyl-3-trifluoromethyl-5-phenylpyrazole, 1-acetyl-5-trifluoromethyl-3-phenylpyrazole, benzotrifluoride, benzoyltrifluoroacetone, 1-benzoyl-3-trifluoromethyl-5-methylpyrazole, 1-benzoyl-5-trifluoromethyl-3-methylpyrazole, 1-benzoyloxy-4-(2,2,2-trifluoroethoxy)benzene, 1-benzoyl-4-trifluoromethylbenzene, 1,4-bis(t-butoxy)tetrafluorobenzene, 2,2-bis(4-methylphenyl)hexafluoropropane, bis(pentafluorophenyl)carbonate, 1,4-bis(1,1,2,2-tetrafluoroethoxy)benzene, 2,4-bis(trifluoromethyl)benzaldehyde, 2,6-bis(trifluoromethyl)benzonitrile, difluoroacetophenone, 2,2-difluorobenzodioxole, 2,2-difluoro-1,3-benzodioxole-4-carbaldehyde, 1-[4-(difluoromethoxy)phenyl]ethanone, 3-(3,5-difluorophenyl)-1-propene, fluorobenzophenone, difluorobenzophenone, 1-(2'-fluoro[1,1'-biphenyl]-4-yl)propan-1-one, 6-fluoro-3,4-dihydro-2H-1-benzothiin-4-one, 4-fluorodiphenyl ether, 5-fluoro-1-indanone, 1-(3-fluoro-4-methoxyphenyl)ethanone, fluorophenylacetonitrile, the group of compounds having an Si—C bond consisting of bis(pentafluorophenyl)dimethylsilane, 1,2-bis[difluoro(methyl)silyl]ethane, N,O-bis(trimethylsilyl)trifluoroacetamide, N-(t-butyldimethylsilyl)-N-methyltrifluoroacetamide, t-butyldimethylsilyl trifluoromethanesulphonate, 2-dimethylamino-1,3-dimethylimidazolium trimethyldifluorosiliconate, diphenyldifluorosilane, the group of compounds having a C=O bond consisting of bis(1,1,1,3,3,3-hexafluoroprop-2-yl) 2-methylenesuccinate, bis(1,1,1,3,3,3-hexafluoroprop-2-yl)maleate, bis(2,2,2-trifluoroethyl)maleate, bis(perfluorooctyl)fumarate, bis(perfluoroisopropyl)ketone, 2,6-bis(2,2,2-trifluoroacetyl)cyclohexanone, butyl 2,2-difluoroacetate, cyclopropyl 4-fluorophenyl ketone, diethyl perfluoroadipate, N,N-diethyl-2,3,3,3-tetrafluoropropionamide, the group of compounds having a C=C bond consisting of allyl 1H,1H-heptafluorobutyl ether, trans-1,2-bis(perfluorohexyl)ethylene, (E)-5,6-difluoroocta-3,7-diene-2-one, the group of amines consisting of N,N-diethyl-1,1,2,3,3,3-hexafluoropropylamine The solvent may also additionally contain benzene, fluorobenzene, toluene, trifluorotoluene, xylene or cyclohexane.

The term "difluoroacetophenone" encompasses the isomers with the fluorine substitution in the 2,3-, 2,4-, 2,5-, 2,6-, 3,4- and 3,5-position on the aromatic ring.

The term "fluorobenzophenone" encompasses in particular the isomers 2-fluorobenzophenone and 4-fluorobenzophenone.

The term "difluorobenzophenone" encompasses the isomers with the fluorine substitution in the 2,3'-, 2,3-, 2,4'-, 2,4-, 2,5-, 2,6-, 3,3'-, 3,4'-, 3,4-, 3,5- and 4,4'-position.

The term "fluorophenylacetonitrile" encompasses the isomers with the fluorine substitution in the 2-, 3- and 4-position.

The compounds can be synthesized in a known manner and are also commercially available, for example from ABCR GmbH & Co. KG, Karlsruhe, Germany.

Preferred fluorinated organic compounds useful as solvents or, preferably, as solvent additives in the electrolyte compositions are selected from the group of fluorosubstituted carboxylic acid esters, fluorosubstituted carboxylic acid amides, fluorosubstituted fluorinated ethers, fluorosubstituted carbamates, fluorosubstituted cyclic carbonates, fluorosubstituted acyclic carbonates, fluorosubstituted phosphites, fluorosubstituted phosphoranes, fluorosubstituted phosphoric acid esters, fluorosubstituted phosphonic acid esters and saturated or unsaturated fluorosubstituted heterocycles.

Suitable fluorinated ethers applicable as solvent or additional additive in the electrolytic compositions are for example those as described in U.S. Pat. No. 5,916,708, namely partially fluorinated ethers of formula (A)

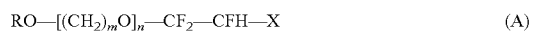

$$RO—[(CH_2)_mO]_n—CF_2—CFH—X \qquad (A)$$

wherein
R is a linear alkyl group with 1 to 10 C atoms or a branched alkyl group with 3 to 10 C atoms,
X is fluorine, chlorine or a perfluoroalkyl group with 1 to 6 C atoms which groups may include ether oxygen,
m is an integer of 2 to 6 and
n is an integer of 1 to 8,
and/or of formula (II)

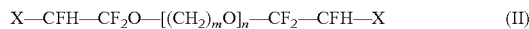

$$X—CFH—CF_2O—[(CH_2)_mO]_n—CF_2—CFH—X \qquad (II)$$

wherein
X, m and n have the meaning given above.

Partially fluorinated carbamates suitable as solvent or additional additives are for example those described in U.S. Pat. No. 6,159,640, namely compounds of the formula $R^1R^2N—C(O)OR^3$ wherein $R^1$ and $R^2$ independently are the same or different, and are linear C1-C6-alkyl, branched C3-C6-alkyl, C3-C7-cycloalkyl, or $R^1$ and $R^2$ are connected directly or via one or more additional N and/or O atoms forming a ring with 3 to 7 members. Optionally, additional N atoms in the ring are saturated with C1 to C3 alkyl groups, and additionally, the carbon atoms of the ring may be substituted by C1 to C3 alkyl groups. In the groups $R^1$ and $R^2$, one or more hydrogen atoms may be substituted by fluorine atoms. $R^3$ is a partially fluorinated or perfluorinated linear or branched alkyl group with 1 to 6 or, respectively, 3 to 6 carbon atoms, or a partially or perfluorinated cycloalkyl group with 3 to 7 C atoms, which may be substituted by one or more C1 to C6 alkyl groups.

Fluorinated acetamides suitable as solvent or additional solvent additive are for example those described U.S. Pat. No. 6,489,064, namely partially fluorinated amide corresponding to formula $R^1CO—NR^2R^3$ wherein $R^1$ is a linear C1-C6 alkyl group in which at least one hydrogen atom is replaced by fluorine, or a branched C3-C6 alkyl group in which at least one hydrogen atom is replaced by fluorine, or a C3-C7 cycloalkyl group optionally substituted one or more times by a linear C1-C6 alkyl group or branched C3-C6 alkyl group or both in which at least one hydrogen atom of the cycloalkyl group or the optional linear or branched alkyl substituent or both is replaced by fluorine, and $R^2$ and $R^3$ independently represent an identical or different linear C1-C6 alkyl group, a branched C3-C6 alkyl group or a C3-C7 cycloalkyl group, or together with the amide nitrogen form a saturated five or six-membered nitrogen-containing ring, or are joined with one or more additional N and/or O atom(s) to form a 4 to 7-membered ring in which the additional N atoms present in the ring are optionally saturated with C1-C3 alkyl groups and the ring carbon atoms may also carry C1-C3 alkyl groups.

Partially fluorinated esters suitable as solvent or solvent additive are for example those described in U.S. Pat. No. 6,677,085 partially fluorinated compound derived from a diol corresponding to the formula $R^1CO—O—[CHR^3(CH_2)_m'O]_n—R^2$ wherein $R^1$ is a (C1-C8) alkyl group or a (C3-C8) cycloalkyl group, wherein each of said groups is partially fluorinated or perfluorinated so that at least one hydrogen atom of the group is replaced by fluorine; $R^2$ is a (C1-C8) alkyl carbonyl or (C3-C8) cycloalkyl carbonyl group, wherein said alkylcarbonyl or cycloalkylcarbonyl group may optionally be partially fluorinated or perfluorinated; $R^3$ is a hydrogen atom or a (C1-C8) alkyl or (C3-C8) cycloalkyl group; m is 0, 1, 2 or 3, and n is 1, 2 or 3.

The electrolyte composition, further to the at least one compound of formula (I), comprises at least one dissolved electrolyte salt. Such salts have the general formula $M_aA_b$. M is a metal cation, and A is an anion. The overall charge of the salt $M_aA_b$ is 0. M is preferably selected from Li$^+$ and NR$_4^+$. Preferred anions are PF$_6^-$, PO$_2$F$_2^-$, AsF$_6^-$, BF$_4^-$, ClO$_4^-$, N(CF$_3$SO$_2$)$_2^-$ and N(i-C$_3$F$_7$SO$_2$)$_2^-$.

Preferably, M is Li$^+$. Especially preferably, M is Li$^+$ and the solution comprises at least one electrolyte salt selected from the group consisting of LiBF$_4$, LiClO$_4$, LiAsF$_6$, LiPF$_6$, LiPO$_2$F$_2$, LiN(CF$_3$SO$_2$)$_2$ and LiN(i-C$_3$F$_7$SO$_2$)$_2$. Lithium bis(oxalato)borate can be applied as an additional additive. The concentration of the electrolyte salt is preferably 1±0.1 molar. Often, the electrolyte composition may comprise LiPF$_6$ and LiPO$_2$F$_2$.

If LiPO$_2$F$_2$ is the only electrolyte salt, its concentration in the electrolyte composition is, as mentioned, preferably 1±0.1 molar. If LiPO$_2$F$_2$ is applied as an additive together with another electrolyte salt, especially together with LiPF$_6$, the concentration of LiPO$_2$F$_2$ in the electrolyte composition preferably is equal to or greater than 0.1% by weight, more preferably equal to or greater than 0.5% by weight; preferably, its concentration is equal to or lower than 10% by weight, more preferably, equal to or lower than 5% by weight when the total electrolyte composition including electrolyte salt, solvent and additives is set as 100% by weight.

Another aspect of the present invention concerns solvent compositions for lithium ion batteries, lithium air batteries or lithium sulfur batteries, containing at least one solvent for lithium ion batteries lithium air batteries or lithium sulfur batteries, and further containing at least one fluorinated derivative of Meldrum's acid having the formula (I)

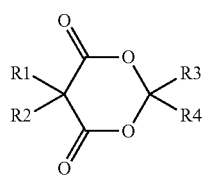

(I)

wherein R1 to R4 independently denote hydrogen, halogen, or linear or branched alkyl group optionally substituted by one or more halogen atoms; provided that at least one of the R1 to R4 is fluorine or fluorinated substituent; and at least one solvent suitable as solvent in Li ion batteries, Li air batteries and Li sulfur batteries; and optionally, at least one solvent additive. Preferred solvents and solvent additives are given above. In the solvent compositions, the amount of the at least one compound of formula (I) is often equal to or greater than 6% by weight the amount of the at least one compound of formula (I) is often equal to or lower than 12% by weight. The amount of additives, if they are present, is preferably equal to or greater than 1% by weight, and is preferably equal to or lower than 12% by weight. The balance to 100% by weight is the at least one solvent.

Another aspect of the present invention are electrolytic compositions comprising at least one compound of formula (I)

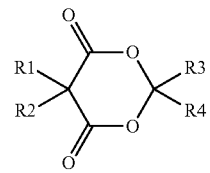

(I)

wherein R1 to R4 independently denote hydrogen, halogen, or linear or branched alkyl group optionally substituted by one or more halogen atoms; provided that at least one of the R1 to R4 is fluorine or fluorinated substituent; an electrolyte salt and optionally at least one further solvent and optionally at least one further additive. Preferably, the electrolyte compositions comprise at least one compound of formula (I), at least one electrolyte salt and at least one solvent and optionally at least one further additive. Preferred compounds of formula (I), preferred electrolyte salts, preferred solvents and preferred additives are those given above.

The compound of formula (I) is contained in the compositions in an amount greater than 0 and preferably equal to or lower than 10% by weight of the total composition. The amount of electrolyte salt is preferably in the range 1±0.1 molar.

The compounds of formula (I) can be introduced into the electrolyte composition separately or in the form of a mixture with other compounds, e.g. as a mixture with a solvent or solvents used in the electrolyte composition or in together with electrolyte salt or other additives.

Still another aspect of the present invention are Li ion batteries, Li air batteries and Li sulfur batteries comprising a solvent composition as outlined above or an electrolyte composition as outlined above.

Should the disclosure of any patents, patent applications, and publications which are incorporated herein by reference conflict with the description of the present application to the extent that it may render a term unclear, the present description shall take precedence.

The following examples are intended to describe the invention in further detail without the intention to limit it.

EXAMPLE 1

Preparation of 5-fluoro-2,2-dimethyl-1,3-dioxane-4,6-dione

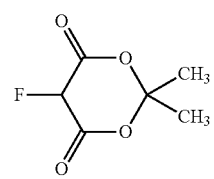

Formula (I-1)

2-fluoromalonic acid diethylester is manufactured from 2-chloromalonic acid diethylester and 1,8-diazabicyclo[5,4,0]undec-7-ene.1,37HF neat at 80° C., as described in example 2 of U.S. Pat. No. 7,145,046. The raw product is hydrolyzed, in analogy to example 1 of DE-Offenlegungsschrift 4120704, by contacting it with NaOH in water (concentration of NaOH: 30% by weight). Resulting ethanol is removed by distillation, and the resulting solution is contacted with Lewatit S 100 in the H-form (i.e. comprising acidic $H^+$). The aqueous solution of fluoromalonic acid is mixed with toluene, and at a reduced pressure (400 mbar), a water/toluene mixture is removed.

The resulting fluoromalonic acid then reacted with acetone as described by D. Davidson and S. A. Bernhard in J. Chem. Soc. 70 (1948), page 3428, 1. paragraph in chapter "Experimental". The fluoromalonic acid is suspended in acetic anhydride and concentrated sulfuric acid is added. The amounts of the reagents and starting compounds correspond to those described by Davidson et al.

The acetone is added under cooling. After a post-reaction phase of 2 hours, 5-fluoro-2,2-dimethyl-1,3-dioxane-4,6-dione can be isolated.

EXAMPLE 2

Preparation of 2,2,5-trifluoro-1,3-dioxane-4,6-dione

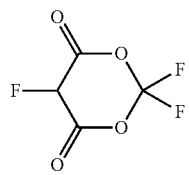

Formula (I-2)

In a first step, fluoromalonic acid (which may be obtained as described in example 1) is reacted with $C(O)Cl_2$ under cooling to 0° C. in the presence of triethylamine. Diethyl ether is added, solids (hydrochloride) are filtered off, low boiling constituents (mainly diethyl ether) are evaporated, and the resulting 2-fluoro-1,3-dioxane-2,4,6-trione is contacted with $SF_4$ in an autoclave for 15 hours. Low boiling contents, e.g. $SOF_2$, are removed from the autoclave in a vacuum, and 2,2,5-trifluoro-1,3-dioxane-4,6-dione may be isolated.

EXAMPLE 3

Alternative Method for the Preparation of 2,2,5-trifluoro-1,3-dioxane-4,6-dione

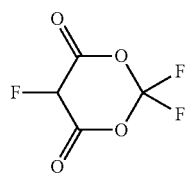

Formula (I-2)

In a first step, malonic acid is reacted with $C(O)Cl_2$ under cooling to 0° C. in the presence of triethylamine. Diethyl ether is added, solids (hydrochloride) are filtered off, low boiling constituents (mainly diethyl ether) are evaporated, and the resulting 1,3-dioxane-2,4,6-trione is suspended in perfluorohexane. A gaseous mixture of $F_2$ in $N_2$ (volume ratio 1:4) is passed through the suspension at a temperature of approximately −20° C. until the molar ratio of $F_2$:1,3-dioxane-2,4,6-trione is about 3:1. The flow of $F_2/N_2$ gas is stopped, and vacuum is applied to remove low boiling constituents, especially HF.

A mixture mainly containing 2,2,5-trifluoro-1,3-dioxane-4,6-dione and 2,5,5-trifluoro-1,3-dioxane-4,6-dione is obtained which can be purified and separated for example by preparative chromatography.

EXAMPLE 4

Manufacture of 5-fluoro-2-trifluormethyl-2-methyl-1,3-dioxane-4,6-dione

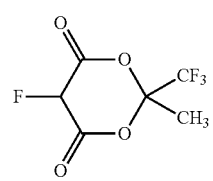

Formula (I-3)

Example 1 is repeated, but instead of acetone, 1,1,1-trifluoroacetone is applied as starting material.

EXAMPLE 5

Manufacture of 5-fluoro-2,2-bistrifluormethyl-1,3-dioxane-4,6-dione

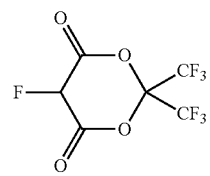

Formula (I-4)

Example 1 is repeated but instead of acetone, hexafluoroacetone is applied as starting material.

EXAMPLE 6

Manufacture of 2,2-bistrifluoromethyl-1,3-dioxane-4,6-dione

Example 5 is repeated, but instead of fluoromalonic acid, malonic acid is applied as starting material.

EXAMPLE 7

Manufacture of Electrolyte Compositions Containing at Least One Compound of Formula (I)

| Compound of formula (I); amount [% by weight] | Solvent [balance to 100% by weight] | Electrolyte salt; amount [mol/l] | Further additive; amount [% by weight] |
|---|---|---|---|
| (I-1); 3 | EC | 1 | — |
| (I-II); 3 | EC | 1 | — |
| (I-III); 3 | EC | 1 | — |
| (I-IV); 3 | EC/ | 1 | — |

-continued

| Compound of formula (I); amount [% by weight] | Solvent [balance to 100% by weight] | Electrolyte salt; amount [mol/l] | Further additive; amount [% by weight] |
|---|---|---|---|
| (I-1); 3 | EC/PC vol/vol 1:1 | 1 | F1EC; 2 |
| (I-1I); 3 | EC/PC vol/vol 1:1 | 1 | LiPOF; 1 |
| (I-1II); 3 | EC/PC vol/vol 1:1 | 1 | — |
| (I-1V); 3 | EC/PC vol/vol 1:1 | 1 | — |
| (I-1); 3 | EC/DMC vol/vol 1:1 | 1 | F1EC; 2 |
| (I-1I); 3 | EC/DMC vol/vol 1:1 | 1 | LiPOF; 1 |
| (I-1II); 3 | EC/DMC vol/vol 1:1 | 1 | — |
| (I-1V); 3 | DMC | 1 | — |
| (I-1); 1.5; (I-2); 1.5; | EC/PC vol/vol 1:1 | 1 | — |
| 2,2-bistrifluoromethyl-1,3-dioxane-4,6-dione; 3 | EC/PC vol/vol 1:1 | 1 | — |
| 2-methyl-2-trifluoromethyl-1,3-dioxane-4,6-dione; 3 | EC/PC vol/vol 1:1 | 1 | — |

Abbreviations:
EC = Ethylene carbonate
DMC = Dimethyl carbonate
PC = Propylene carbonate
F1EC = fluoroethylene carbonate
LiPOF = $LiPO_2F_2$ The electrolyte compositions are prepared by mixing appropriate amounts of the compound or compounds of formula (I), the solvent or solvents, the electrolyte salt and additives if applied in a vessel which is dried beforehand and through which dry $N_2$ is passed to prevent an atmosphere which is dry and free of oxygen.

The invention claimed is:

1. An electrolyte composition for lithium ion batteries, lithium air batteries or lithium sulfur batteries, containing at least one solvent and at least one electrolyte salt and a compound having formula (I):

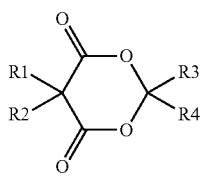

Formula (I)

wherein R1 and R2 independently denote hydrogen, halogen, or linear or branched alkyl group optionally substituted by one or more halogen atoms; and wherein R3 and R4 independently denote halogen, or linear or branched alkyl group optionally substituted by one or more halogen atoms; provided that at least one of the R1 to R4 is fluorine or fluorinated substituent.

2. A lithium ion battery containing a compound having formula (I):

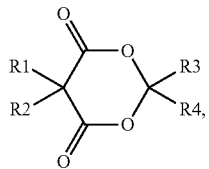

Formula (I)

wherein R1 and R2 independently denote hydrogen, halogen, or linear or branched alkyl group optionally substituted by one or more halogen atoms; and wherein R3 and R4 independently denote halogen, or linear or branched alkyl group optionally substituted by one or more halogen atoms; provided that at least one of the R1 to R4 is fluorine or fluorinated substituent.

3. The lithium ion battery according to claim 2, wherein R1 and R2 independently denote hydrogen, fluorine, or linear or branched alkyl group optionally substituted by one or more fluorine atoms; and wherein R3 and R4 independently denote fluorine, or linear or branched alkyl group optionally substituted by one or more fluorine atoms; provided that at least one of the R1 to R4 is fluorine or fluorinated substituent.

4. The lithium ion battery according to claim 3, wherein R1 is fluorine.

5. The lithium ion battery according to claim 4 wherein R2 is hydrogen or fluorine.

6. The lithium ion battery according to claim 5, wherein R3 and R4 are independently selected from the group consisting of fluorine, methyl, monofluoromethyl, difluoromethyl and trifluoromethyl.

7. The lithium ion battery according to claim 5, wherein the compound has formula (I-1), (I-2), (I-3) or (I-4):

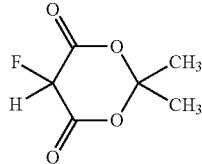

Formula (I-1)

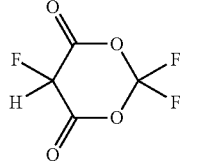

Formula (I-2)

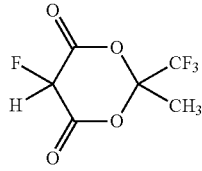

Formula (I-3)

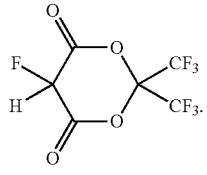

Formula (I-4)

8. The electrolyte composition according to claim 1, wherein R1 and R2 independently denote hydrogen, fluorine, or linear or branched alkyl group optionally substituted by one or more fluorine atoms; and wherein R3 and R4 independently denote fluorine, or linear or branched alkyl group optionally substituted by one or more fluorine atoms; provided that at least one of the R1 to R4 is fluorine or fluorinated substituent.

9. The electrolyte composition according to claim 8, wherein R1 is fluorine.

10. The electrolyte composition according to claim 9 wherein R2 is hydrogen or fluorine.

11. The electrolyte composition according to claim 10, wherein R3 and R4 are independently selected from the group consisting of fluorine, methyl, monofluoromethyl, difluoromethyl and trifluoromethyl.

12. The electrolyte composition according to claim 10, wherein the compound has formula (I-1), (I-2), (I-3) or (I-4):

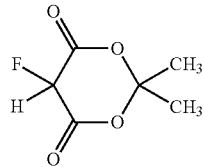

Formula (I-1)

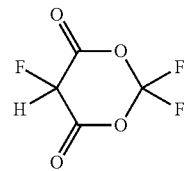

Formula (I-2)

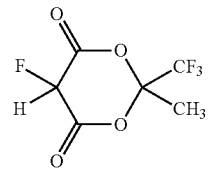

Formula (I-3)

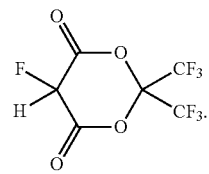

Formula (I-4)

* * * * *